United States Patent [19]

Arganbright et al.

[11] 4,032,583
[45] June 28, 1977

[54] PURIFICATION OF 1,4-BUTANEDIOL

[75] Inventors: Robert P. Arganbright, Seabrook; William G. Bowman, Pasadena, both of Tex.

[73] Assignee: Petro-Tex Chemical Corporation, Houston, Tex.

[22] Filed: Aug. 8, 1975

[21] Appl. No.: 602,986

[52] U.S. Cl. .......................... 260/637 R; 260/635 D
[51] Int. Cl.[2] ........................................ C07C 29/24
[58] Field of Search .................... 260/637 R, 643 D

[56] References Cited
UNITED STATES PATENTS

| | | | |
|---|---|---|---|
| 3,088,982 | 5/1963 | Feldman et al. | 260/643 D |
| 3,705,925 | 12/1972 | Starks et al. | 260/643 D |
| 3,898,291 | 8/1975 | Darsi et al. | 260/643 D |
| 3,917,720 | 11/1975 | Webb et al. | 260/637 R |

OTHER PUBLICATIONS

Large "Handbook of Chemistry," 10th Ed., (1961), pp. 508 and 509.

Primary Examiner—Joseph E. Evans
Attorney, Agent, or Firm—Kenneth H. Johnson; N. Elton Dry

[57] ABSTRACT

An improved process is disclosed for recovering 1,4-butanediol in high purity from a mixture comprising 1,4-butanediol in admixture with minor amounts of certain impurities which comprises diluting the 1,4-butanediol-containing mixture with water to form an aqueous mixture having from about 5 to about 75 wt. % water and contacting said aqueous mixture in an extraction zone with a hydrocarbon extractant. An aqueous 1,4-butanediol-containing raffinate is obtained as the bottoms product of the extraction zone and is introduced into a distillation zone operated at reduced pressure from which substantially pure 1,4-butanediol is recovered.

9 Claims, 1 Drawing Figure

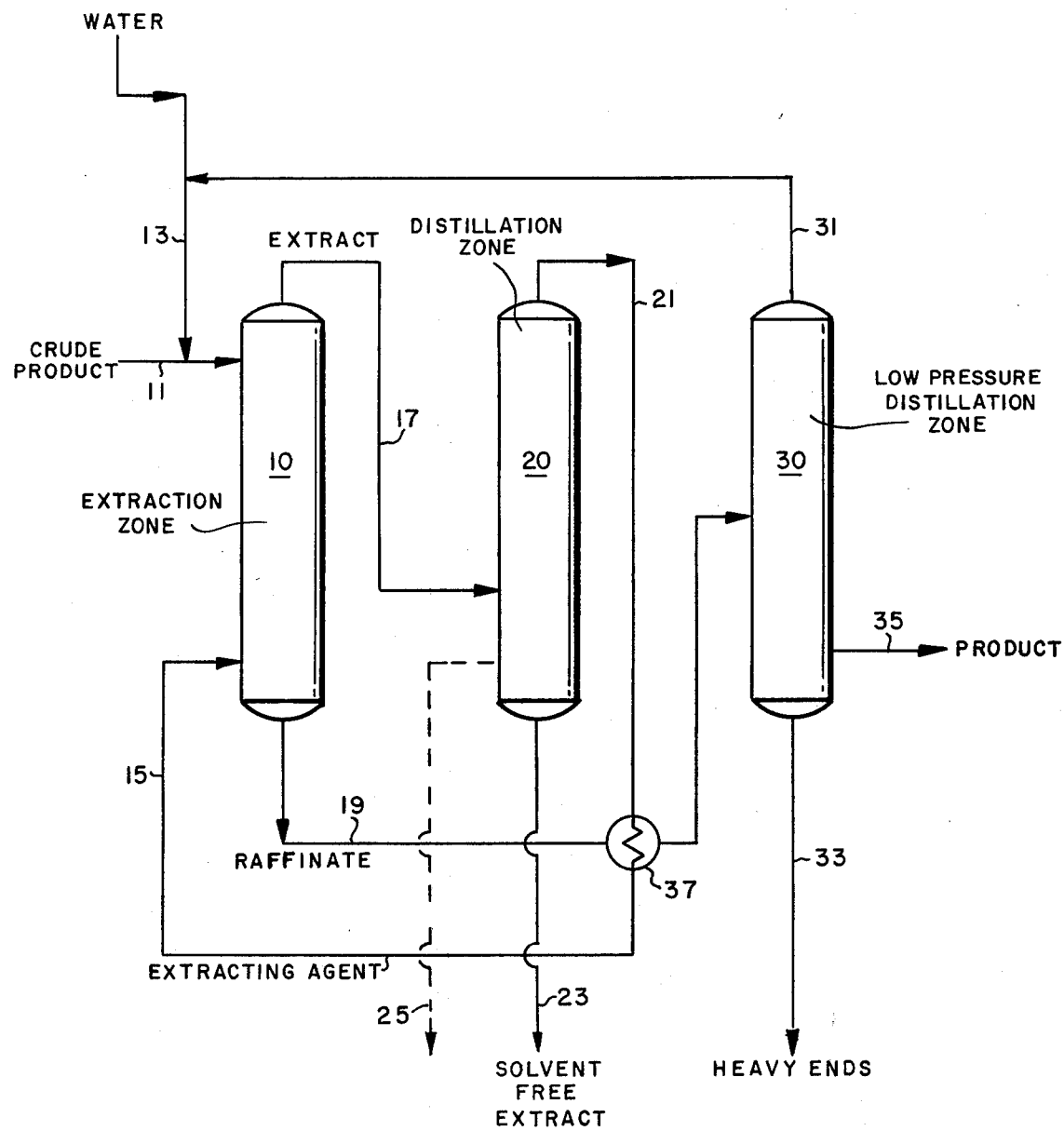

4,032,583

PURIFICATION OF 1,4-BUTANEDIOL

BACKGROUND OF THE INVENTION

1. Field Of The Invention

This invention relates to an improved method of separating glycols from crude glycol mixtures additionally containing dialkyl esters of such glycols. More particularly, this invention relates to a method of separating 1,4-butanediol from a crude 1,4-butanediol-containing mixture obtained as a result of hydrogenation of a mixture of dialkyl maleate and dialkyl fumarate.

2. Description Of The Prior Art 1,4-butanediol is a monomer used in the production of polybutylene terephalate, a unique engineering plastic. Butanediol has been manufactured commercially by processes involving the Reppe reaction of acetylene and formaldehyde followed by hydrogenation of the reaction mixture. Other processes for the production of 1,4-butanediol involve the hydrolysis of dichorobutanes or the hydrogenation of maleic anhydride.

Processes for the production of 1,4-butanediol from maleic acid or maleic anhydride generally involve esterification of the maleic precursor to a dialkyl ester from which 1,4-butanediol is obtained by hydrogenation. The crude butanediol product obtained by hydrogenation of such dialkyl esters of maleic acid contains the desired 1,4-butanediol in admixture with uncoverted dialkyl maleate, dialkyl fumarate and other by-products which are formed in the hydrogenation of the ester and which are impurities in the 1,4-butanediol product.

Recovery of substantially pure 1,4-butanediol by conventional distillation is impractical since the unreacted ester will co-distill with the desired diol product. Also impurities contained in the crude butanediol product obtained from the hydrogenation reaction such as alkyl succinate and alkyloxy alkyl succinate form azeotropic mixtures with the desired 1,4-butanediol. For example, dibutyl succinate and 1,4-butanediol form an azeotrope containing 40% dibutyl succinate. Likewise, dibutyl butoxy succinate forms an azeotrope with 1,4-butanediol containing approximately 10% dibutyl butoxy succinate. Therefore, 1,4-butanediol cannot be obtained in high purity from feedstocks containing such impurities using conventional distillation techniques.

SUMMARY OF THE INVENTION

In accordance with the instant invention, 1,4-butanediol is recovered in high purity from a mixture comprising 1,4-butanediol in admixture with minor amounts of one or more impurities selected from the group of dibutyl maleate and dibutyl fumarate, dibutyl succinate, γ-hydroxybutyraldehyde, γ-butyrolactone and dibutyl butoxy succinate, in a process comprising diluting the 1,4-butanediol-containing mixture with water to form an aqueous mixture having from about 5 to about 75 wt. % water and thereafter intimately contacting the aqueous mixture in an extraction zone with a hydrocarbon extracting agent. An aqueous 1,4-butanediol-containing raffinate is obtained from the extraction zone with a substantially reduced impurity content, from which substantially pure 1,4-butanediol is recovered in a distillation zone at reduced pressure.

BRIEF DESCRIPTION OF THE FIGURE

The invention will be illustrated by reference to the attached FIGURE which represents a schematic flow diagram of a preferred embodiment of the invention.

DESCRIPTION OF THE PREFERRED EMBODIMENT

In accordance with the present invention, a crude 1,4-butanediol-containing mixture, obtained from the hydrogenation of a mixture of dialkyl esters of maleic acid, e. g. dibutyl maleate and dibutyl fumarate, is subjected to a process in which the impurities are extracted from the butanediol-containing mixture resulting in 1,4-butanediol being obtained in high purity. The crude butanediol-containing mixtures which are the object of this invention, are generally obtained as the reaction product from the hydrogenation of dialkyl esters of maleic acid. Whenever the dialkyl esters are the dibutyl esters, the following compounds are generally found in such crude butanediol mixtures in the following approximate concentrations:

| | | |
|---|---|---|
| dibutyl succinate and dibutyl fumarate | 2.0–5.0 | mole% |
| dibutyl butoxysuccinate | 1.0–3.0 | mole% |
| γ-butyrolactone | 1.0–3.0 | mole% |
| γ-hydroxybutyraldehyde | 1.0 | mole% |
| Butoxy-1,4-butanediol | 2.0–4.0 | mole% |
| High boiling residues | 4.0–8.0 | wt.% |

In addition to the above impurities, there may be considerable quantities of butanol present; however, the major proportions of butanol generally will be removed from the crude butanediol-containing mixture, for example by distillation, before such butanediol-containing mixture is subjected to the process of this invention. It will be apparent to one skilled in the art, that although the foregoing description of the impurities present in a crude butanediol-containing mixture relate to butyl derivatives of maleic acid, this reflects merely the choice of alcohol used in the initial esterification reaction. It is equivalently useful to produce crude butanediol-containing mixtures from dialkyl esters of maleic acid in which other monohydric alcohols were employed in the esterification reaction. For example, any monohydric alcohol which forms an zeotrope with water is suitable for practice in the process of preparing dialkyl esters of maleic acid from which such crude butanediol-containing mixtures are obtained. Illustrative monohydric alcohols include ethanol, propanol, butanol, amyl alcohol, and the like. Butanol is a preferred monohydric alcohol employed in preparing the dialkyl esters from which the crude butanediol-containing mixture, which is the subject of this invention, is prepared.

According to the process of this invention, the crude 1,4-butanediol-containing mixture is diluted with water to form an aqueous mixture having a water content of from about 5 to about 75 wt. % water, and preferably from about 20 to about 50 wt. %. It has been found that adding water to the crude butanediol-containing mixture improves the phase separation obtained between the aqueous phase and the hydrocarbon extract phase in the extraction zone. Moreover, maintaining a water concentration within the aforementioned range results in an improved extraction of impurities into the hydrocarbon extract phase.

In the extraction zone, the aqueous 1,4-butanediol-containing mixture is contacted with a hydrocarbon extracting agent which is immiscible with the aqueous butanediol-containing mixture. Suitable hydrocarbon extracting agents which may be employed in practicing the process of this invention include alkanes having from about 6 to about 10 carbon atoms and aromatic hydrocarbons having from about 6 to about 8 carbon atoms. Examples of suitable hydrocarbon extracting agents include hexane, heptane, octane, benzene, toluene, and the like. It is preferable to select a hydrocarbon extracting agent with a relatively low boiling point, in that the hydrocarbon extract phase recovered from the extraction zone is subjected to a distillation to recover the hydrocarbon extracting agent. In this manner, it is possible to minimize the energy requirements necessary for the practice of this invention. For this reason, hexane and benzene are particularly preferred extracting agents.

In the extracting zone, the aqueous 1,4-butanediol-containing mixture is contacted with the extracting agent to effect the extraction of the impurities into the hydrocarbon extract phase. Thereafter, the two phases are separated. This extraction step can be effected by a variety of known methods. For example, rotating disc contactor may be employed to effect the extraction, alternately, the aqueous butanediol-containing mixture and the extracting agent may be intimately mixed by suitable mixing device and thereafter separated as for example by centrifugation or in a suitable setting zone which may include packing material in order to facilitate separation of the phases. A preferred embodiment of this invention which is illustrated in FIG. 1, illustrates a continuous process, wherein the aqueous 1,4-butanediol-containing mixture is introduced at the top of the extraction zone and the extracting agent is introduced at the bottom of the extraction zone. The flow of the two streams is countercurrent through the extraction zone wherein they are brought into intimate contact to effect the desired extraction of impurities from the aqueous 1,4-butanediol-containing mixture.

The ratio of hydrocarbon extracting agent to aqueous butanediol-containing mixture will vary depending upon the amount of impurities contained in the aqueous butanediol mixture and the disired degree of removal desired. Generally, a volumetric ratio of aqueous 1,4-butanediol to hydrocarbon extracting agent of from about 5:1 to about 1:5 is generally satisfactory, with a ratio of about 2:1 to about 1:2 being preferred. In one embodiment of the process of this invention, the extraction is carried out in a single extraction stage; however, alternate embodiments of the process of this invention involve the deployment of a plurality of extraction zones numbering from 2 to about 5. In such extractions involving multiple extractions zones, it is generally preferable to have countercurrent flow of the hydrocarbon extracting agent. Fresh hydrocarbon extracting agent is contacted with the aqueous 1,4-butanediol-containing mixture in the last extraction stage and the recovered hydrocarbon extract phase is then flowed to the preceeding extraction stage, and so forth. It is equivalently useful to employ parallel flow of the hydrocarbon extracting agent, in which the flow of the hydrocarbon extracting agent is divided such that fresh hydrocarbon extracting agent is contacted with the aqueous 1,4-butanediol mixture in each of the extraction stages.

The temperature at which the extraction of impurties from the aqueous butanediol-containing mixture is effected is not critical. The optimum temperature will depend upon the choice of extracting agent and the nature and quantity of the impurities being extracted. Generally, a temperature in the extraction zone of from 25° to about 100° C. is generally satisfactory, with a temperature of about 25° to about 50° C. being preferred. The pressure at which the extraction zone is operated is generally any pressure at which the two liquid streams are maintained in the liquid state. Pressures of from about atmospheric pressure to 50 psig are adequate for this purpose, although higher pressures may be employed if desired.

The hydrocarbon extract phase which is recovered from the extraction zone will generally contain γ-hydroxybutyraldehyde, γ-butyrolactone, dibutyl fumarate, dibutyl succinate, dibutyl butoxy succinate, and a non-volatile residue. A small proportion of n-butanol may also be present if the initial distillation of the crude hydrogenation zone product is not efficient. This hydrocarbon extract phase is generally subjected to a distillation to recover the hydrocarbon extracting agent for reuse in the process of this invention. A solvent-free extract is obtained from the bottom of the distillation zone and may be recycled to the hydrogenation zone of a process for converting maleic acid esters to butanediol. Inasmuch as this bottoms product from the solvent recovery zone will contain a considerable proportion of non-volatile residue, it is preferable to take a slip stream representing a portion of this stream and subjecting it to further recovery steps to remove the heavy material. Alternately, a bottoms product may be recovered from the solvent recovery zone which comprises substantially the non-volatile residue and the bulk of the other aforementioned impurities may be recovered as a side draw product from a portion of the solvent recovery zone above the bottom.

The raffinate phase recovered from the extraction zone comprises 1,4-butanediol, water and a small proportion of some of the more difficult to remove impurities such as γ-butyrolactone and butoxy-1,4-butanediol. This raffinate is introduced to a low pressure distillation zone in which the water is recovered as an overhead product. Any non-volatile residue remaining in the raffinate phase is recovered as a bottoms product from the low pressure distillation zone. 1,4-butanediol is recovered as a side draw product in high purity and substantially free of water. The pressure at which the low pressure distillation zone is operated should be such that the temperature in the bottom of the distillation zone does not exceed about 150° C. At higher temperatures there is an increased degradation of the 1,4-butanediol product which increases the difficulty of obtaining 1,4-butanediol in high purity. The low pressure distillation zone should be operated subtantially to exclude the presence of air. Oxygen is known to cause degradation of 1,4-butanediol at elevated temperatures. Therefore, care should be taken in order to ensure that the leakage of air into the low pressure distillation zone is minimized. In embodiments of the process of this invention, in which the low pressure distillation is carried out in a batch process, it is preferable to blanket the distillation zone with an inert gas, such as nitrogen.

Now reference will be made to the attached FIGURE which represents a schematic flow diagram of a preferred embodiment of the present invention wherein 1,4-butanediol is recovered from a crude 1,4-butanediol-containing mixture in an extraction zone employing a hydrocarbon extracting agent. The raffinate recovered from the extraction zone is introduced into a low pressure distillation zone to recover 1,4-butanediol in high purity. It is to be understood that the FIGURE is only a schematic representation of the process and does not purport to show the conventional instrumentation present in a typical process.

A crude 1,4-butanediol mixture additionally containing impurities carried by line 11 is diluted with water carried by line 13 to provide an aqueous butanediol-containing mixture having a water content of from about 5 to about 75 wt. %. The aqueous mixture is introduced into the upper portion of extraction zone 10 wherein it is contacted with a hydrocarbon extracting agent in order to remove the impurities from the aqueous butanediol-containing mixture. The hydrocarbon extracting agent is introduced into a lower portion of the extraction zone 10 by line 15. An extract phase containing the impurities extracted from the aqueous butanediol-containing mixture is recovered from the extraction zone 10 in line 17 a raffinate phase containing the aqueous 1,4-butanediol-containing mixture of reduced impurity level is recovered from the extraction zone 10 in line 19.

The hydrocarbon extract phase is carried by line 17 to an intermediate portion of a distillation zone 20 wherein the hydrocarbon extracting agent is recovered as an overhead product in line 21. A substantially solvent-free extract is recovered from a bottom portion of distillation zone 20 in line 23. The solvent-free extract comprises the impurities extracted from the crude 1,4-butanediol-containing mixture. Typically, the solvent-free extract stream is recycled to the hydrogenation zone of the process wherein the crude 1,4-butanediol is obtained. Inasmuch as the impurities extracted from the crude butanediol product will include a non-volatile residue which is also recovered in distillation zone 20, in one embodiment of the process of this invention it is preferable to recover the substantially solvent-free extract as a side draw from the distillation zone 20 in line 25 as is illustrated in phantom. In such embodiment, the non-volatile residue is recovered from the bottom of distillation zone 20 in line 23.

The raffinate from the bottom of extraction zone 10 is carried via line 19 to an intermediate portion of a low pressure distillation zone 30. In the low pressure distillation zone 30 substantially all of the water contained in the raffinate is recovered as an overhead product in line 31 which is combined with line 13 to provide the water necessary to dilute the crude 1,4-butanediol-containing product as hereinbefore described. A non-volatile residue containing stream is recovered as a bottom product from the low pressure distillation zone 30 in line 33. 1,4Butanediol is recovered from a side draw of the low pressure distillation zone 30 via line 35.

The operating pressure of the low pressure distillation zone 30 is approximately 15–20 mm Hg which results in a comparatively low bottoms temperature of about 150° C. In this manner, thermal degradation of the 1,4-butanediol is minimized. The thermal energy required for the low pressure distillation is provided by conventional means, e.g. a reboiler not shown in the attached FIGURE. The raffinate stream carried via line 19, which is the feed to low pressure distillation zone 30, is passed through heat exchanger 37 wherein it exchanges heat with the overhead product from distillation zone 20 carried via line 21. In this manner, the overall thermal efficiency of the process is maximized.

The above invention is characterized in that the process results in the removal of a substantial proportion of the impurities which make recovery of 1,4-butanediol in high purity impracticable in a normal distillation process. By this invention 1,4-butanediol is obtained in "polymergrade" high purity as is required for its use in the porduction of polybutylene terephthalate and tetrahydrofuran.

The invention will now be illustrated by the following examples which are for the purposes of illustration and should not be considered a limitation on the scope of the invention.

EXAMPLE 1

In this example, 300 g of crude 1,4-butanediol was diluted with 300 g of water and subjected to three extractions employing 100 ml of hexane in each extraction. The composition of the crude butanediol and the final purified 1,4-butanediol after the three extractions are presented in the following Table 1. The breakdown of the percent removal of contaminants in each of the three extraction stages is presented for two of the key components, dibutyl succinate and butoxy dibutyl succinate.

TABLE 1

|  | Crude 1,4-butanediol | Product 1,4-butanediol* |
| --- | --- | --- |
| n-butyl alcohol | 4.39 | Trace |
| γ-butyrolactone | 0.26 | 0.24 |
| 1,4-butanediol | 87.27 | 95.17 |
| γ-hydroxybutyraldehyde | 0.32 | 0.39 |
| dibutyl succinate | 2.62 | Trace |
| 2-butoxy-1,4-butanediol | 4.08 | 4.20 |
| butoxy dibutyl succinate | 0.86 | Trace |

*water excluded from the analysis

|  | % Ester Removed per Extraction | | |
| --- | --- | --- | --- |
|  | 1st | 2nd | 3rd |
| dibutyl succinate | 89.0 | 10.0 | 0.9 |
| butoxy dibutyl succinate | 90.0 | 9.7 | Trace |

The aqueous product 1,4-butanediol obtained from the three extractions was subjected to a low pressure distillation to remove the water. 1,4-butanediol with a purity of approximately 99.7% and uncontaminated with ester was obtained as a final product. In this distillation, 259 g of the crude 1,4-butanediol were distilled in a 1 inch × 33 inch distillation column with an operating pressure of 15 mm Hg. A number of cuts were obtained throughout the distillation and analyzed for 1,4-butanediol and impurities. The data are presented in the following Table 2, which data does not include the proportion of water in the overhead cuts. The data indicate that approximately 66% of the crude 1,4-butanediol is recoverable as a high purity 1,4-butanediol product. By comparison, a low pressure distillation was attempted with a crude 1,4-butanediol mixture which had not been subjected to the extraction process of this invention. The data for this distillation is presented in the following Table 3. From an analysis of the data contained therein, it is apparent that approximately only 10% of the 1,4-butanediol contained in the crude diol mixture was recoverable in a purity exceeding 95%.

In a comparable extraction employing benzene as the hydrocarbon extracting agent, 61% of the 1,4-butanediol was recovered from the raffinate in a purity exceeding 99.5%.

TABLE 2

Distillation Of Hexane Extracted 1,4-Butanediol

Distribution of Components, Wt.%.

| Cut No. | Wt. g. | Total % Ovhd. | Pot Temp. °C. | n-Butyl Alcohol | unknown | γ-Butyro-Lactone | 1,4-Butane-diol | (γ-Hydroxy-butyral-dehyde) | Dibutyl Succinate | Dibutyl Fumarate |
|---|---|---|---|---|---|---|---|---|---|---|
| 1 | 15 | 5.8 | 151 | 0.15 | .02 | 1.24 | 95.8 | 2.6 | 0.10 | 0.07 |
| 2 | 17.5 | 12.6 | 151 | 0.03 | | 0.17 | 98.8 | 1.0 | | |
| 3 | 16.0 | 18.8 | 151 | 0.03 | | 0.44 | 99.3 | 0.5 | | |
| 4 | 5.5 | 20.9 | 151 | 0.20 | | 0.64 | 98.6 | 0.7 | | |
| 5 | 14.0 | 26.3 | 153 | 0.10 | | 0.94 | 98.2 | 0.7 | | |
| 6 | 15.0 | 32.1 | 153 | 0.05 | | 0.24 | 99.5 | 0.4 | | |
| 7 | 18.0 | 39.0 | 154 | 0.07 | | 0.19 | 99.7 | 0.03 | | |
| 8 | 15.0 | 44.8 | 155 | 0.05 | | 0.19 | 99.7 | 0.05 | | |
| 9 | 17.0 | 51.4 | 155 | 0.07 | | 0.22 | 99.7 | | | |
| 10 | 13.0 | 56.4 | 155 | 0.05 | .01 | 0.24 | 99.7 | | | |
| 11 | 12.5 | 61.2 | 155 | 0.06 | .02 | 0.18 | 99.8 | | | |
| 12 | 15.5 | 67.2 | 155 | 0.11 | .11 | 0.56 | 99.2 | | | |
| Undist. Fract. | 85.0 | | | | | | | | | |

TABLE 3

| Cut No. | Wt. g. | H₂O | THF | n-Butyl Alcohol | Dibutyl Formal | γ-Butyro-lactone | 1,4-Butane Diol | γ-Hydroxy Butyral-dehyde | Dibutyl Succinate | Dibutyl Maleate | Butoxy-1,4-butane-Diol | Butoxy dibutyl Succinate | Unknown |
|---|---|---|---|---|---|---|---|---|---|---|---|---|---|
| 1 | 52.0 | 31.7 | 1.6 | 63.2 | 0.1 | | | | | | | | 3.4 |
| 2 | 125.0 | 0.9 | | 98.9 | 0.09 | | | | | | | | |
| 3 | 139.0 | 0.3 | | 99.7 | 0.03 | | | | | | | | 0.04 |
| 4 | 388.5 | | | 99.9 | | | | | | | | | |
| 5 | 13.0 | | | 49.1 | 17.2 | 6.4 | | | | | | | 27.3 |
| 6 | 18.0 | 0.2 | | 3.2 | | 63.2 | 13.9 | 12.6 | | | | | 7.0 |
| 7[1] | 60.9 | | | 1.1 | | 4.2 | 6.1 | 0.6 | 85.3 | 0.2 | | | 2.6 |
| 8 | 18.7 | | | 3.5 | | 6.4 | 71.5 | 2.5 | 14.8 | 0.3 | | 1.0 | |
| 9 | 26.4 | | | | | 1.6 | 88.1 | 3.4 | 4.1 | 0.2 | | 2.6 | |
| 10 | 25.0 | | | 1.5 | | 1.7 | 84.6 | 0.7 | 1.1 | 0.5 | | 9.8 | |
| 11 | 30.5 | | | 0.2 | | 2.2 | 84.5 | 0.8 | | | | 12.1 | |
| 12 | 36.0 | | | 0.3 | | 0.5 | 91.6 | 0.4 | | | | 7.2 | |
| 13 | 37.0 | | | 0.5 | | 0.7 | 87.4 | 0.2 | | 0.2 | | 11.4 | |
| 14 | 36.5 | | | 0.2 | | 0.5 | 94.0 | 0.1 | | | | 5.2 | |
| 15 | 25.7 | | | 0.3 | | 0.4 | 97.1 | trace | | | | 2.2 | |
| 16 | 22.2 | | | 0.6 | | 0.2 | 98.0 | | | | | 1.2 | |
| 17 | 34.7 | | | 0.2 | | 0.2 | 99.6 | 0.04 | | | | | |
| 18 | 29.6 | | | 0.3 | | 0.3 | 98.7 | trace | | | 0.4 | | 0.3 |
| Btms Col.[2] | 68.0 | | | | | 0.2 | 19.2 | 0.5 | | | 80.2 | | |
| Hold-up | 15.0 | | | | | | 99.0 | | | | | | |
| Total Wt. | | 18.1 | 0.8 | 693.2 | 18.6 | 332.6 | 3.1 | 58.4 | 0.4 | 54.6 | 17.1 | | |
| Mole% Comp. Excl. of n-Butyl Alcohol and Unk. | | | | | 0.2 | 4.97 | 79.89 | 0.86 | 5.40 | 0.4 | 7.34 | 1.30 | |

[1] Top phase removed from continuous decantor
[2] Composition of column holdup assumed to be 99% diol.

EXAMPLE 2

To a mixture of 10 g of water and 16.9 g of crude 1,4-butanediol (88.8% by weight butanediol, 5.79% butyrolactone and 5.34% butyl succinate) was added 10 g of benzene. The mixture was mixed and the benzene phase allowed to separate. The benzene phase consisted of 1.93% butyrolactone, 0.38 butanediol, 6.21% butyl succinate and 91.46% benzene. From this data, it can be seen that 19.4% of the butyrolactone and 67.32% of the butyl succinate were extracted from the starting blend. Only 0.24% of the butanediol was extracted with the benzene extracting agent.

EXAMPLE 3

By a procedure similar to that of Example 2, a crude 1,4-butanediol-containing mixture was subjected to five extractions with equal volumes of benzene. The extraction was done on the crude 1,4-butanediol mixture after removing any butyl alcohol. The data in the following Table 4 demonstrate that a very high percentage removal of esters are achieved from the crude diol mixture. It is also apparent that benzene is particularly effective in removing γ-hydroxybutyraldehyde and γ-butyrolactone from the crude diol mixture.

TABLE 4

| | Crude 1,4-butanediol | Raffinate Phase, g. | Extract Phase, g. |
|---|---|---|---|
| 1,4-Butanediol | 600.9 | 594.0 | 6.9 |
| γ-Hydroxybutyraldehyde | 4.0 | 0.36 | 3.6 |
| γ-Butyrolactone | 23.1 | 4.2 | 18.9 |
| dibutyl Fumarate | 45.7 | — | 45.7 |
| dibutyl Succinate | 56.6 | 0.03 | 56.6 |
| dibutyl Butoxysuccinate | 34.6 | 0.05 | 34.6 |
| Butoxy-1,4-butanediol | 47.0 | 45.8 | 1.2 |
| Non-volatile residue | 70.8 | 22.2 | 48.6 |
| | 882.7 | 666.64 | 216.1 |

The high purity 1,4-butanediol product had the following properties:

TABLE 4

| Freeze point | 20.1° C. |
|---|---|
| Initial color, Hazen | 10 |
| Water content (C. Fisher method) | 0.08 |
| After heating 4 hrs. at 190–195° C. Color | 10 |

TABLE 4-continued

| | |
|---|---|
| Odor | None |
| Water (C. Fisher) | 0.16 |

We claim as our invention:

1. In a process for recovering 1,4-butanediol in high purity from a mixture comprising 1,4-butanediol in admixture with minor amounts of one impurties selected from the group of dibutyl succinate, dibutyl fumarate, dibutyl maleate, γ-hydroxybutyraldehyde, dibutyl butoxy succinate and γ-butyrolactone, the improvement which comprises
   a. adding water to said mixture in an amount to produce an aqueous 1,4-butanediol-containing mixture having from about 5 to about 75 weight percent water,
   b. intimately contacting said aqueous 1,4-butanediol-containing mixture in an extraction zone with a hydrocarbon extracting agent selected from the group of alkanes of from 6 to about 10 carbon atoms, aromatic hydrocarbons of from 6 to about 10 carbon atoms, and mixtures thereof, in an amount such that the volumetric ratio of the aqueous 1,4-butanediol-containing mixture to the hydrocarbon extracting agent is from about 5:1 to about 1:5,
   c. allowing the contacted aqueous 1,4-butanediol-containing mixture and the hydrocarbon extracting agent to separate whereby there is formed an extract phase containing the bulk of said impurities and an aqueous 1,4-butanediol-containing raffinate of reduced impurity content,
   d. recovering said extract phase from said extraction zone,
   e. recovering said raffinate from said extraction zone,
   f. introducing said raffinate into a distillation zone operated at reduced pressure and recovering substantially pure 1,4-butanediol from a lower portion of the distillation zone.

2. The process according to claim 1, wherein water is added to the 1,4-butanediol-containing mixture in an amount to produce an aqueous 1,4-butanediol-containing mixture having from about 20 to about 50 weight percent water.

3. The process according to claim 2, wherein the volumetric ratio of the aqueous 1,4-butanediol-containing mixture to hydrocarbon extracting agent is from about 2:1 to about 1:2.

4. The process according to claim 2, wherein the hydrocarbon extracting agent is an alkane having from about 6 to about 10 carbon atoms.

5. The process according to claim 4, wherein the extracting agent is hexane.

6. The process according to claim 2, wherein the extracting agent is an aromatic hydrocarbon selected from the group of benzene, toluene and the xylenes.

7. The process according to claim 6, wherein the extracting agent is benzene.

8. The process according to claim 1, wherein the contacting of the aqueous 1,4-butanediol-containing mixture and the hydrocarbon extracting agent is effected in a plurality of extraction zones numbering from 2 to about 5 in which the hydrocarbon extracting agent is introduced into each of the extraction zones and contacted therein with the raffinate recovered from the preceeding extraction zone.

9. The process according to claim 1, wherein the contacting of the aqueous 1,4butanediol-containing mixture and the hydrocarbon extracting agent is effected in a plurality of extraction zones numbering from 2 to about 5 in which the aqueous 1,4-butanediol is flowed in series from zone to zone with the hydrocarbon extracting agent being introduced into the last of said extraction zones and the extract phase being recovered and flowed in series from zone to zone in countercurrent flow to the raffinate phase.

* * * * *

UNITED STATES PATENT OFFICE
CERTIFICATE OF CORRECTION

PATENT NO. : 4,032,583                                Page 1 of 2

DATED      : June 28, 1977

INVENTOR(S) : Robert P. Arganbright & William G. Bowman

It is certified that error appears in the above-identified patent and that said Letters Patent are hereby corrected as shown below:

List of References, right hand column, 2nd line, reads "Large" but should read -- Lange --

Column 1, line 15 reads "terephalate" but should read -- terephthalate --

Column 1, lines 29-30 reads "uncoverted" but should read -- unconverted --

Column 2, line 46 reads "zeotrope" but should read -- azeotrope --

Column 3, line 30 reads "setting" but should read -- settling --

Column 3, line 45 reads "disired" but should read -- desired --

Column 5, line 23 reads "17 a raffinate" but should read -- 17 and a raffinate --

Column 6 line 9 reads "porduction" but should read -- production --

UNITED STATES PATENT OFFICE
CERTIFICATE OF CORRECTION

PATENT NO. : 4,032,583
DATED : June 28, 1977
INVENTOR(S) : Robert P. Arganbright & William G. Bowman It is certified that error appears in the above-identified patent and that said Letters Patent are hereby corrected as shown below:

Column 9, line 9, Claim 1 reads "of one impurties" but should read -- of one or more impurities --

Column 10, line 31, Claim 9 reads "1,4butanediol" but should read -- 1,4-butanediol --

Signed and Sealed this

Eleventh Day of March 1980

[SEAL]

Attest:

SIDNEY A. DIAMOND

Attesting Officer          Commissioner of Patents and Trademarks